United States Patent
Sibner

(10) Patent No.: US 6,846,182 B1
(45) Date of Patent: Jan. 25, 2005

(54) DENTAL BLEACHING COMPOSITION AND METHOD

(76) Inventor: Jeffrey A. Sibner, 333 Oxford Valley Rd., Suite 106, Fairless Hills, PA (US) 19030

( * ) Notice: Subject to any disclaimer, the term of this patent is extended or adjusted under 35 U.S.C. 154(b) by 396 days.

(21) Appl. No.: 09/114,166

(22) Filed: Jul. 13, 1998

Related U.S. Application Data

(63) Continuation-in-part of application No. PCT/US97/21273, filed on Nov. 26, 1997, which is a continuation-in-part of application No. 08/757,248, filed on Nov. 27, 1996, now Pat. No. 5,766,011.

(51) Int. Cl.$^7$ .................................................. A61K 6/00
(52) U.S. Cl. .................... 433/215; 433/216; 433/203.1; 433/217.1; 424/52; 424/53; 106/35
(58) Field of Search ................................ 433/215, 216, 433/217.1, 203.1; 424/53, 52, 710, 714, 688, 693; 106/35

(56) References Cited

U.S. PATENT DOCUMENTS

| | | | | |
|---|---|---|---|---|
| 4,582,701 A | * | 4/1986 | Piechota, Jr. ................. | 424/52 |
| 4,661,070 A | * | 4/1987 | Friedman .................... | 433/215 |
| 4,687,663 A | * | 8/1987 | Schaeffer .................... | 424/52 |
| 4,877,401 A | * | 10/1989 | Higuchi et al. ............. | 433/215 |
| 4,983,381 A | * | 1/1991 | Torres Zaragoza ........... | 424/53 |
| 5,009,885 A | * | 4/1991 | Yarborough .................. | 424/53 |
| 5,032,178 A | * | 7/1991 | Cornell ........................ | 106/35 |
| 5,041,280 A | * | 8/1991 | Smigel ........................ | 424/52 |
| 5,123,845 A | * | 6/1992 | Vassiliadis et al. ......... | 433/215 |
| 5,306,143 A | * | 4/1994 | Levy ........................... | 43/215 |
| 5,318,562 A | * | 6/1994 | Levy et al. ................... | 606/16 |
| 5,409,631 A | * | 4/1995 | Fischer ........................ | 424/53 |
| 5,645,428 A | * | 7/1997 | Yarborough ................. | 433/215 |

* cited by examiner

*Primary Examiner*—Gene Mancene
*Assistant Examiner*—Cary E. O'Connor
(74) *Attorney, Agent, or Firm*—Karen Lee Orzechowski; IP Law Specialists, LLC

(57) ABSTRACT

A dental bleaching composition having enhanced effectiveness and reduced sensitivity, its method of use, and a kit containing the ingredients for making the composition. The dental bleaching composition comprises a bleaching agent, an inert gelling agent, a pH modifying agent, a discrete inert particulate laser enhancing material, and optionally a transparency modifying agent in the form of a gel with a pH of about 9.5 to 11. The dental bleaching composition is placed on the teeth to be bleached, exposed to laser light for a desired period of time, and removed. The process is then repeated for one or more cycles until the desired degree of bleaching is achieved. Neutral sodium fluoride is then applied to the bleached teeth for at least 10 minutes to reduce or eliminate post-bleaching sensitivity.

34 Claims, No Drawings

DENTAL BLEACHING COMPOSITION AND METHOD

CROSS-REFERENCE TO RELATED APPLICATIONS

This application is a continuation-in-part of International Patent Application No. PCT/US97/21273 filed on Nov. 26, 1997, which in turn is a continuation-in-part of U.S. patent application Ser. No. 08/757,248 filed on Nov. 27, 1996, now issued as U.S. Pat. No. 5,766,011.

FIELD OF THE INVENTION

The present invention relates to dental bleaching compositions and methods, and more particularly to novel dental bleaching compositions and methods utilizing a laser to dramatically enhance the bleaching action. The invention more particularly relates to dental bleaching compositions and methods with enhanced removal of both extrinsic and intrinsic discolorants from the dentition and with reduced pain or sensitivity associated with the bleaching process.

BACKGROUND OF THE INVENTION

Discolorations, or stains, of the dentition are traditionally classified into two main categories, extrinsic and intrinsic. Extrinsic discolorations are on the outer surface of the dentition and can be removed from the surface through the use of dental instruments or polishing abrasives. In contrast, intrinsic discolorations are located within the crystalline matrix of the enamel and dentin and are not removable through the use of conventional dental instruments or polishing abrasives.

Extrinsic discolorations or stains are usually superficial stains of the tooth surface resulting from the deposition of a film, pigments or calculus on the teeth. Many agents can cause such extrinsic discolorations including common substances such as coffee, tea, artificial food colorations, grapes, berries, smoking or chewing of tobacco, and the like. Stain intensity, and consequently ease of removal of the stains, are worsened by the penetration of the stain into tooth surface irregularities such as pits, cracks, grooves, exposed dentin, and bared root surfaces resulting from recession. The degree of difficulty of removal of the stain increases the deeper the penetration of the stain, with some stains penetrating to such a depth that the removal is extremely difficult or virtually impossible using current methods of stain removal.

Intrinsic discolorations can have many causes of either an endogenous or exogenous origin and may occur during or after odontogenesis. During the process of creation of the teeth, referred to as odontogenesis, the teeth may become discolored from changes in the quality or quantity of enamel or dentin, or from incorporation of discoloring agents in the hard tissues, and may be caused by many diseases and medications, such as tetracycline. Post-eruption discolorations occur when discoloring agents enter the dental hard tissues from either the pulp cavity or tooth surface and can be caused by trauma, aging, metals, dental materials, and contact with or ingestion of certain foods and beverages.

A commonly practiced technique for removing discoloration is the practice of external bleaching, often with hydrogen peroxide. However, known bleaching agents are able only to remove discoloring agents located within five to seven microns from the enamel surface due to the high inorganic content and limited permeability of the enamel. Thus intrinsic discolorations and deeply penetrating extrinsic discolorations are left untouched.

Many attempts have been made over the years to find a bleaching system capable of removing intrinsic and deeply penetrating extrinsic stains. Chemical reagents that have been tried include hydrogen peroxide, oxalic acid, pyrozone (hydrogen peroxide and ethyl ether), muriatic acid, and chlorine compositions, as well as bleaching agents such as a 30% superoxol (30% hydrogen peroxide stabilized by reducing the pH to 4.0–5.0) or a pyrozone (30% hydrogen peroxide and ethyl ether) used in conjunction with heat from a light source, such as a tungsten lamp, or a heated instrument or bleaching paddle. The addition of heat to accelerate hydrogen peroxide's bleaching action has made such systems capable of reacting fast enough for in-office use. However, side effects due to the increased reactivity can be quite painful and include inflamed or burned gingiva and lips, as well as significant post-bleaching tooth sensitivity.

In an effort to overcome these side effects, "cold bleaching" systems were developed. These systems used longer room temperature reaction times instead of shorter heat activated reaction times. In these cold bleaching systems, the hydrogen peroxide is thickened or gelled to allow the hydrogen peroxide to form a coating capable of remaining in contact with the teeth for an extended period of time. Although the cold bleaching systems eliminated the side effects of the application of heat, a number of office visits were still required to achieve satisfactory results and post-bleaching sensitivity still occurred.

Recently, as disclosed in U.S. Pat. No. 5,645,428 to Yarborough, lasers have been used in a two-step dental bleaching process in which first an admixture of a bleaching agent and a catalyst are applied to the teeth and then exposed to an argon laser light to activate the bleaching agent followed by a second application of an admixture of a bleaching agent and a catalyst followed by exposure to a $CO_2$ laser. However, the use of the $CO_2$ laser adds considerable cost to the process as well as greatly increasing the chances of incurring damage to the enamel surface of the teeth due to exposure to the $CO_2$ laser.

SUMMARY OF THE INVENTION

It has now been unexpectedly discovered that the novel dental bleaching composition of the present invention can be used in conjunction with a laser to provide dramatically enhanced and highly effective bleaching action on both extrinsic and intrinsic discolorations and stains while reducing or eliminating damage to the mouth tissues and post-bleaching sensitivity.

The novel dental bleaching composition comprises a bleaching agent such as hydrogen peroxide, carbamine peroxide and the like; an inert gelling compound, preferably a silica gelling agent such as fumed silica or silicon dioxide compound; a pH modifier such as sodium hydroxide; and a discrete inert particulate laser enhancing material. These materials are admixed to form a translucent or transparent gel with a pH of about 9 to 12, more preferably from about 9.5 to about 11.0, and most preferably from about 10 to 10.5. The discrete particles are capable of absorbing the light energy from the wavelength of light emitted from the laser and retransmitting it as thermal energy. These discrete particles are dispersed throughout the bleaching composition so that the laser beam can pass through to the surface of the tooth while the particles absorb a portion of the light energy from the laser and retransmit it as thermal energy thus increasing the effectiveness of the bleaching composition. Additional translucency of the silicon-dioxide based bleaching composition may be provided by the addition of a transparency modifying agent such as glycerin.

The novel dental bleaching composition of present invention is used by placing it on the tooth surfaces to be bleached, to thoroughly coat and cover the area of the tooth surface to be bleached. The coated tooth surfaces are exposed to laser energy for the desired exposure time, and then the coating is removed from the tooth surfaces, preferably by rinsing. The process is then repeated for one or more cycles until the desired degree of bleaching of the dental surface is achieved. Neutral sodium fluoride is then applied to the bleached teeth for at least 10 minutes to reduce or eliminate post-bleaching sensitivity.

A kit containing the ingredients allows single dose applications to be mixed immediately before use.

DETAILED DESCRIPTION OF THE INVENTION

The present invention is directed to novel dental bleaching compositions that provide dramatically enhanced and highly effective bleaching action while reducing or eliminating mouth tissue damage and post-bleaching sensitivity. In a preferred embodiment of the present invention, the topical dental bleaching compositions include a bleaching agent, an inert gelling agent for forming a gel with said bleaching agent, a plurality of discrete laser enhancing particles, and a pH modifier. The discrete inert laser enhancing particles absorb a portion of the light energy emitted by the laser by means of the color of the particles, the composition of the particles, or by combinations thereof and retransmit it as thermal energy. The particles are present in an amount sufficient to enhance the activity of the bleaching agent and still allow light from the laser to penetrate the bleaching composition to reach the surface of the tooth.

The topical dental bleaching composition of the present invention is preferably in the form of a gel to allow coating of the tooth surfaces with minimal contact with the gums and mouth tissue to reduce exposure and sensitivity thereof. The gel is formed from admixing a bleaching agent with an inert gelling compound. The pH of the gel is modified or adjusted to about 9 to 12, more preferably from about 9.5 to about 11.0, and most preferably from about 10 to 10.5, to reduce post-bleaching sensitivity. To enhance the effectiveness of the bleaching composition, discrete inert laser enhancing particles are dispersed throughout the composition.

The bleaching agent may be any bleaching agent suitable for use on dentition in living patients. Preferably the bleaching agent is a peroxide such as hydrogen peroxide or carbamine peroxide. Other suitable bleaching agents may include sodium perborate, oxalic acid (for iron stains), chlorine (for silver and copper stains), and ammonia (for iodine-containing stains).

In the most preferred embodiment of the present invention, the bleaching agent is hydrogen peroxide in concentrations ranging from about 5% to about 70% by volume, more preferably from about 25% to about 60% by volume, and most preferably from about 35% to about 50% by volume. The amount of hydrogen peroxide present is about 75% to about 95% by weight, preferably from about 90% to about 95% by weight, of the total mixture.

Any suitable inert composition can be used that is capable of forming a gel or thickened mixture when admixed with the bleaching agent. Suitable gelling compositions include silica compounds, sodium stearate, and long chain hydrocarbons such as Carbopol™, Trolamine™ and Polyox™. In a preferred embodiment of the present invention, an inert silica compound is used and suitable silica compounds include silicon dioxide, fumed silica and the like. Preferably the silica compound is in a finely divided form that enhances the gelling reaction with the hydrogen peroxide. The preferred concentration of the silica gelling agent is approximately 5 to 10% by weight.

Bleaching agents, such as hydrogen peroxide, are concentration-dependant pulpal irritants. The higher the concentration of bleaching agent placed on the surface of a tooth, the more rapidly the concentration of bleaching agent rises within the enamel and dentin of the tooth. Even at lower concentrations, bleaching agents can irritate the pulp causing pulpitis and at higher concentrations, can cause pulpal death. However, using too low of a concentration of bleaching agent will result in ineffective bleaching of the extrinsic and intrinsic discolorations on the tooth.

One embodiment of the present invention is directed to the discovery that even with very high concentrations of hydrogen peroxide, post-bleaching tooth and dental sensitivity can be significantly decreased. It has been unexpectedly discovered that post-bleaching tooth and dental sensitivity can be reduced or eliminated by adjusting or modifying the pH of the bleaching composition to at least 9.0, and more preferably between 10.5 to 11.0. Any suitable pH modifier can be used. In one embodiment of the present invention, sodium hydroxide (NaOH) or sodium polysilicate is used to adjust the pH. Further reduction in post-bleaching sensitivity can be achieved by maintaining hydration of the dental tissues during the bleaching process and thus eliminating pulpitis and its attendant sensitivity.

Any suitable laser light source can be utilized in the practice of the present invention and the use of the novel dental bleaching compositions claimed herein. In a preferred embodiment of the present invention, a laser capable of increasing the bleaching action of a bleaching agent on a tooth surface, such as an argon or diode laser, is used to enhance the bleaching action of the dental bleaching composition. Theoretically, the laser light enhances the speed by which enamel and dentin can be bleached by any or all of the following mechanisms: i) lowering the energy needed to break down the stain molecules within the teeth, ii) pushing the bleaching gel into the tooth more rapidly, and iii) interacting with the bleaching gel to enhance its reactivity. It has been unexpectedly discovered that teeth coated with the topical dental bleaching compositions of the present invention and exposed to laser light bleach significantly lighter than teeth of the same shade bleached with the a bleaching gel composition alone. This effect is dependent on the strength of the dental bleaching composition and the strength of the laser light. For example, an argon laser yielding a power density of 550–700 milliwatts/cm$^2$ bleaches the coated tooth surfaces more effectively than a laser yielding a power density of 350–550 milliwatts/cm$^2$ but at the cost of increased sensitivity during and following the bleaching process. This may be due to one or both of the following mechanisms i) the laser energy "pushes" the hydrogen peroxide into the tooth more rapidly—the concentration of hydrogen peroxide at any distance from the surface of the tooth may be greater when the tooth is bathed in argon laser light than in the absence of the laser, and ii) the laser energy may contribute directly to pulpal irritation.

In a preferred embodiment of the present invention, the bleaching action of the dental bleaching composition is enhanced by the inclusion into the bleaching composition of a discrete inert particulate laser enhancing material capable of absorbing the wavelength of light emitted by the laser. In a preferred embodiment of the invention, the discrete inert particulate laser enhancing material is pigmented or colored in a color complement to the laser light, thus resulting in efficient absorption of the laser light wavelength. For example, an argon laser utilizes a blue light with a wavelength in the range of 470 nm to 520 nm. The color complement to blue is orange, and thus an orange or red-orange colored or pigmented particulate material that reflects light in the 600 nm to 650 nm range and absorbs at all other wavelengths would be suitable. Also preferred are other colors that absorb at the wavelength of the laser light being utilized. For example, a black particulate material would absorb all wavelength of emitted light an thus would be suitable. In another preferred embodiment of the present invention, discrete inert particulate materials that are of a chemical composition or physical arrangement that results in absorption of the laser light and conversion of the absorbed laser light into thermal energy are utilized in the bleaching composition of the present invention. For example, an inert plastic material that absorbs light at a wavelength of 470 nm to 520 nm would be useful as the discrete particulate material of the present invention with an argon laser.

There are no studies that show hydrogen peroxide and other bleaching agents are activated or made more reactive directly by exposure to laser energy. However, it has been discovered that the inclusion of a discrete inert particulate material that absorbs the emitted laser light and transforms it into thermal energy renders the bleaching agent more reactive when exposed to an intense light, such as that emitted by a laser. As discussed above, discrete inert particulate material of the appropriate color, composition, or combinations thereof allow the absorption of laser light in an efficient manner resulting in its retransmission as thermal energy. In the micro-environment surrounding each of the particle making up the discrete inert particulate material, this increase in thermal energy renders the bleaching agent more reactive.

The discrete inert particulate material can be made of any suitable material that will not react with the bleaching agent and that will not leach its color or any components of the material into the tooth surface or the bleaching gel during the bleaching process. Suitable materials include materials such as porcelain, ceramic, thermoplastic or polymeric resins such as acrylic resins, cellulosic resins, ceramic fiber compounds, fluoroplastic resins, polyamide resins, polycarbonate resins, phenolic resins, polyethelene resins, polyester resins, polymethylpentene resins, polyoxymethylene resins, polyphenylene resins, polypropylene resins, polystryrene resins, polyvinyl resins, nitrile resins, terephthalic resins, or glass fiber compounds, that either alone or in combination with a coating, coloring or pigmenting of a suitable color absorbs the wavelength of the emitted laser light and retransmits it as thermal energy. Furthermore, other types of plastics and polymeric materials known to those in the art may be used provided that they do not react. Those materials that are not capable of absorbing the laser light or that weakly absorb the laser light may be coated, colored or pigmented with a suitable color that enhances and increases the absorption of the laser light to provide sufficient absorption. The material may be coated, colored or pigmented by any suitable means or process and such coating, coloring and pigmenting means and processes are well known in the art.

The size of the particles can vary and preferably range from about 50 microns to about 350 microns, and more preferably from about 100 microns to about 200 microns.

The amount or density of the particles in the bleaching gel is sufficient to allow the laser to enhance the reactivity of the bleaching agent. However, the particulate density or amount is not so great that it blocks a sufficient amount of laser light from reaching the surface of the tooth. As described above, it is necessary for the laser light to reach the tooth in order to enhance the bleaching action of the bleaching agent since this appears to be the more important part and thus the density of the particulate material need to be adjusted accordingly.

In a further embodiment of the present invention, a transparency modifying agent such as glycerin may be added to the topical bleaching composition to impart further transparency to the topical bleaching composition so as to enable the laser light to more readily reach the surface of the tooth. The amount of transparency modifying agent will depend upon the desired degree of transparency with higher concentrations resulting in greater transparency but also diluting the resultant hydrogen peroxide concentration.

In another embodiment of the present invention, post-bleaching sensitivity is further reduced by the application of neutral sodium fluoride to the bleached teeth for at least ten minutes. Fluoride has been used in dentistry to reduce sensitivity for many years. Often, when the root surface of teeth is exposed to the oral cavity due to gingival recession, these teeth become sensitive to hot, cold and sometimes sweets. Fluoride has been shown to reduce this sensitivity by combining with the crystalline structure of the tooth to form fluorapatite and by blocking dentinal tubuals. It has been discovered that the application of neutral sodium fluoride for at least ten minutes following bleaching teeth with a bleaching agent in conjunction with exposure to laser light, significantly reduces or eliminates the intense pain that otherwise results. This post bleaching pain usually has an onset of about 2 hours post-bleaching and lasts for 2 or more days. When neutral sodium fluoride is applied to the teeth for 5 minutes post bleaching, the pain level is often diminished and lasts for only 8 to 12 hours. When neutral sodium fluoride is applied to the bleached teeth for at least 10 minutes after bleaching is completed, post-bleaching sensitivity is almost completely eliminated.

Further understanding of the present invention can be had by resort to the following example:

EXAMPLE 1

A bleaching composition was made by first mixing silicon dioxide with orange coated glass bead discrete laser enhancing particles, then mixing in hydrogen peroxide to form a gel. A pH modifier was added to adjust the pH to 9.5. The bleaching composition was applied to six maxillary anterior teeth, canine to canine. The teeth were exposed, in turn, to 40 seconds of argon laser light per tooth. The teeth were rinsed with water every 3 to 5 minutes during the bleaching procedure to keep them hydrated.

On three teeth, the bleaching gel was wiped away with a cotton gauze and on the other three teeth, the bleaching gel was rinsed away and the teeth were bathed in water for approximately 20 seconds. The bleaching gel was then replaced and the cycle was repeated for a total of six cycles. Patients reported significantly less pain during and after the bleaching procedure on the teeth that were hydrated. When the sides were switched and the teeth that had been bathed in water were wiped clean instead, while the teeth that were wiped were hydrated, the patients reported that the teeth that were sensitive had switched as well.

The treated teeth were compared with the untreated teeth using a tooth shade indicating device. The treated teeth were significantly whiter than the untreated teeth by an order of several shades.

The dental bleaching composition of the present invention can be supplied to dental practitioners in the form of a kit containing ingredients sufficient for either individual or multiple treatments. The ingredients can be supplied individually in separate containers or vials, or can have multiple ingredients premixed so that the hydrogen peroxide containing mixture can be admixed by the dental professional with the silicon compound at the point of use. In one embodiment, it is contemplated that the dental professional will be supplied with a kit containing a bleaching agent, an inert gelling agent, a pH modifying agent and the discrete inert particulate material, with optionally a transparency modifying agent. All items are packaged with a protocol by which safe and effective use of the materials can be achieved.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A topical dental bleaching composition for use with a laser, said composition comprising
   a bleaching agent,
   an inert gelling agent for forming a gel with said bleaching agent,
   a plurality of discrete laser enhancing particles, and
   a pH modifier.
2. The dental bleaching composition of claim 1 wherein said discrete inert laser enhancing particles absorb a portion of the light energy emitted by the laser and retransmit it as thermal energy.
3. The dental bleaching composition of claim 2 wherein laser light is absorbed by means of the color of the particles, the composition of the particles, or by combinations thereof.
4. The dental bleaching composition of claim 1 wherein said discrete laser enhancing particles are a complementary color to the color of the light emitted by the laser.
5. The dental bleaching composition of claim 2 wherein said particles have a size from about 50 to about 400 microns.
6. The dental bleaching composition of claim 5 wherein said particles have a size from about 75 to about 200 microns.
7. The dental bleaching composition of claim 6 wherein said particles have a size from about 90 to about 125 microns.
8. The dental bleaching composition of claim 3 wherein said particles are coated with the color.
9. The dental bleaching composition of claim 3 wherein the particles contain the color dispersed throughout the particles.
10. The dental bleaching composition of claim 1 for use with a laser emitting a blue light, wherein said particles are orange glass beads having a diameter from about 90 to about 125 microns.
11. The dental bleaching composition of claim 3 wherein said particles are color coated beads having a diameter from about 90 to about 125 microns.
12. The dental bleaching composition of claim 2 wherein the particles are made of a material selected from the group consisting of colored or coated porcelain, ceramic, thermoplastic resins, polymeric resins, acrylic resins, cellulosic resins, ceramic fiber compounds, fluoroplastic resins, polyamide resins, polycarbonate resins, phenolic resins, polyethylene resins, polyester resins, polymethylpentene resins, polyoxymethylene resins, polyphenylene resins, polypropylene resins, polystyrene resins, polyvinyl resins, nitrile resins, terephthalic resins, and glass fiber compounds.
13. A dental bleaching composition of claim 2 wherein said particles are present in an amount sufficient to enhance the activity of the bleaching agent.
14. The dental bleaching composition of claim 2 wherein said particles are present in an amount such that light from the laser can penetrate the bleaching composition to reach the surface of the tooth.
15. The dental bleaching composition of claim 1 wherein the bleaching agent is selected from the group consisting of hydrogen peroxide, carbamine peroxide, sodium perborate, oxalic acid, chlorine, and ammonia.
16. The dental bleaching composition of claim 1 wherein the bleaching agent is hydrogen peroxide.
17. The dental bleaching composition of claim 16 wherein said hydrogen peroxide preferably has a concentration from about 5% to about 70% by volume.
18. The dental bleaching composition of claim 17 wherein said hydrogen peroxide more preferably has a concentration from about 25% to about 60% by volume.
19. The dental bleaching composition of claim 18 wherein said hydrogen peroxide more preferably has a concentration from about 35% to about 50% by volume.
20. The dental bleaching composition of claim 1 wherein the pH is from about 9 to about 12.
21. The dental bleaching composition of claim 20 wherein the pH is from about 9.5 to about 11.
22. The dental bleaching composition of claim 1 wherein the pH is from about 10.0 to about 10.5.
23. The dental bleaching composition of claim 20 wherein the pH modifier is selected from the group consisting of sodium hydroxide and sodium polysilicate.
24. The dental bleaching composition of claim 1 wherein said inert gelling agent is selected from the group consisting of silica compounds, sodium stearate, and long chain hydrocarbons.
25. The dental bleaching composition of claim 24 wherein said inert gelling agent is a silicon dioxide compound.
26. The dental bleaching agent of claim 25 wherein said inert gelling agent is a mixture of silicon dioxide and glycerin.
27. The dental bleaching agent of claim 21 wherein said inert gelling agent is fumed silica.
28. A dental bleaching composition with reduced post-bleaching sensitivity, said composition comprising:
   hydrogen peroxide;
   a thickening agent that forms a gel when mixed with said hydrogen peroxide;
   a pH modifier to adjust the pH of the composition from about 9.5 to about 10.5; and
   discrete inert light absorbing particles.
29. The dental bleaching composition of claim 28 wherein said pH modifier is selected from the group consisting of sodium hydroxide and sodium polysilicate.
30. A dental bleaching system for use with a laser, said system comprising:
   a hydrogen peroxide solution having a concentration of about 35% to 60% by volume:
   a pH modifying agent selected from the group consisting of sodium hydroxide and sodium polysilicate;
   a gelling agent selected from the group consisting of an inert silicon compound capable of forming a gel when admixed with said hydrogen peroxide, fumed silica, a mixture of a silicon dioxide compound and glycerin, and mixtures thereof, and discrete inert colored particles in a color complementary to the color of the laser.

31. The dental bleaching system of claim 30 for use with an argon laser wherein said discrete particulate material is orange.

32. The dental bleaching system of claim 30 for use with a diode laser emitting a blue light of wavelength 520–220 nm wherein said discrete particulate material is orange.

33. A kit for preparing a dental bleaching composition for use with a laser, said kit comprising:

a bleaching agent;

a pH modifying agent selected from the group consisting of sodium hydroxide and sodium polysilicate;

an inert gelling composition capable of forming a gel when admixed with said bleaching agent;

glycerin; and discrete inert laser enhancing particles.

34. The kit of claim 33 wherein said bleaching agent is a hydrogen peroxide solution having a concentration of about 35% to 60% by volume.

* * * * *